United States Patent [19]

Bonneau

[11] 4,300,569
[45] Nov. 17, 1981

[54] RED BLOOD CELL LABELLING KIT

[75] Inventor: Paul-Emile Bonneau, Montreal, Canada

[73] Assignee: Merck & Co., Inc., Rahway, N.J.

[21] Appl. No.: 124,166

[22] Filed: Feb. 25, 1980

Related U.S. Application Data

[62] Division of Ser. No. 903,448, May 8, 1978.

[30] Foreign Application Priority Data

Jun. 17, 1977 [CA] Canada ................... 280764

[51] Int. Cl.$^3$ .......................... A61K 43/00; A61B 5/00
[52] U.S. Cl. ........................................ 128/654; 424/1
[58] Field of Search ............................... 128/653–655, 128/659; 424/1, 1.5

[56] References Cited

U.S. PATENT DOCUMENTS

| | | | |
|---|---|---|---|
| 3,743,714 | 7/1973 | Deutsch | 424/1 |
| 4,027,005 | 5/1977 | Adler et al. | 424/1 |
| 4,042,677 | 8/1977 | Molinski et al. | 128/654 |
| 4,054,645 | 10/1977 | Hill et al. | 424/1 |
| 4,070,493 | 1/1978 | Nadeau | 424/1 |
| 4,087,516 | 5/1978 | Laidler et al. | 424/1 |
| 4,115,541 | 9/1978 | Subramanian et al. | 424/1 |

OTHER PUBLICATIONS

*J. Nucl. Med.*, vol. 17, No. 6, 1976, pp. 565–566.
*J. Nucl. Med.*, vol. 17, No. 10, pp. 941–942.
*J. Nucl. Med.*, vol. 17, No. 11, p. 1027.
*Nucl. Med.*, vol. 18, No. 3, (1977) pp. 305–308.
J. Nucl. Med., Bd XVI/Heft 1, (1977) pp. 26–29.
*Nucl. Med.*, Bd XV/Heft 5, (1976) pp. 211–213.

*Primary Examiner*—C. Fred Rosenbaum
*Attorney, Agent, or Firm*—Thomas E. Arther; Mario A. Monaco

[57] ABSTRACT

This invention relates to a method for efficiently labelling red blood cells, which permits the imaging of blood pools in the intact animal or human patient, accomplished by injection of a saline solution of an alkaline earth metal salt of glucoheptonic acid and a nontoxic stannous salt followed by injection with a solution of sodium pertechnetate Tc 99 m to tag the red blood cells. The invention also relates to the kit used in the method of our invention consisting of a single vial containing 25 mg. calcium glucoheptonate and 3 mg. of stannous chloride dihydrate in 2 ml. of saline solution.

4 Claims, No Drawings

RED BLOOD CELL LABELLING KIT

This is a division of application Ser. No. 903,448, filed May 8, 1978.

BACKGROUND OF THE INVENTION

One of the methods employed in the past to image the blood pool for diagnostic purposes involves the intravenous administration of 99m Tc serum albumin which is available commercially and is a sterile pyrogen-free solution of albumin labelled with Technetium 99m having an activity of greater than 100 microcuries/ml.

In utilizing this method of blood pool imaging, it is important to predose the patient immediately prior to the attempted visualization of the blood pool, since the 99m Tc serum albumin is very rapidly lost from the blood stream by exchange in the kidney.

Another method used in the past for imaging blood pools is the in vitro labelling of red blood cells (outside the host animal) followed by reinjection of the cells into the vascular system of the selected animal. By this method, it is possible to visualize both heart blood pools plus major peripheral vessels up to 3 hours after injection of the labelled cells. As can be seen, this is a complicated procedure, and therefore is a more time-consuming and expensive method.

Still another procedure for imaging blood involves the injection of stannous pyrophosphate followed by injection of 99m Tc-pertechnetate. This technique is reported as successful in producing satisfactory imaging of blood pools.

DESCRIPTION OF THE INVENTION

In accordance with the present invention, there is provided a diagnostic kit suitable for the radioactive labelling of red blood cells in vivo, thus making possible the imaging of blood pools within the circulatory system of the patient being examined. As an integral part of the diagnostic kit of the present invention, there is also provided a novel chemical composition comprising a lyophilized mixture of a glucoheptonate salt and a stannous salt in the ratio of 25 parts by weight of glucoheptonate salt to 3 parts by weight of stannous salt measured as calcium glucoheptonate and stannous chloride dihydrate or approximately 22.9 parts of glucoheptonate ion to 1.32 parts of tin calculated as available stannous ion.

An important feature of the present invention is the provision of an individual diagnostic kit containing a stannous salt capable of supplying an amount of stannous ion equivalent to at least 2.5 mg. and no more than 4.0 mg. of stannous chloride.dihydrate. Less than 2.5 mg. of the stannous chloride does not provide sufficient stannous ion to effect a satisfactory degree of labeling of red blood cells. Because of the known toxicity of stannous salts, no more than 4 mg. of stannous chloride dihydrate or a stannous salt containing an equivalent amount of stannous ion should be incorporated in an individual dosage kit.

The present invention also includes the process for the preparation of the novel chemical composition and the diagnostic method for imaging blood pools in patients suspected of having abnormalities in the circulatory system.

In accordance with the process of the present invention, a sterile solution of a non-toxic, pharmaceutically acceptable salt of glucoheptonic acid, e.g., calcium glucoheptonate, is mixed with a non-toxic stannous salt in a ratio of 25 parts by weight of glucoheptonate salt to 3 parts by weight of stannous salt, calculated as calcium glucoheptonate and stannous chloride dihydrate.

The solution is adjusted to a neutral pH 6–8, subdivided, and lyophilized to produce individual vials containing a dry, sterile mixture comprising 25 mg. calcium glucoheptonate and 3 mg. stannous chloride.dihydrate.

In utilizing the kit of the present invention for imaging the blood pools of a patient to diagnose abnormalities in the cardiovascular system, a vial containing the dry, sterile mixture of calcium glucoheptonate and stannous chloride dihydrate is reconstituted by mixing with 2–8 ml. of a USP saline solution. The reconstituted solution is then used for injection of the patient to be examined. After a period of 30 minutes, a second injection of 2–8 ml. of a sterile saline solution of sodium pertechnetate is made. Following the injection of sodium pertechnetate, it is possible, after waiting from 30 seconds to 2 minutes, to image the blood pools in the patient being examined. This "in vivo" labeling of the red blood cells is exceptionally stable and approximately 95% of the radioactivity is retained by the red blood cells for at least 6 hours following injection. This simple procedure avoids the instability of the human serum albumin/99m Tc injection of the prior art as well as the expense and inconvenience of the in vitro labeling of the red blood cell noted as an alternate prior art method.

EXAMPLE 1

Blood Pool Imaging Kit

A solution is prepared under sterile conditions with 25 g. of calcium glucoheptonate in sterile, pyrogenfree water which has been purged with nitrogen. The solution of calcium glucoheptonate is stored and purged under nitrogen. In a separate container, 3 g. of stannous chloride dihydrate is dissolved in 1 ml. of hydrochloric acid, and the resulting solution diluted with nitrogen purged, sterile water to a volume of 10 ml. The stannous chloride dihydrate solution is then added to the calcium glucoheptonate with stirring and flushing with nitrogen. The solution is mixed thoroughly, and the pH is adjusted to neutrality with a solution of sterile 1N sodium hydroxide solution. The volume is then adjusted to 2000 ml. with sterile, nitrogen purged water and subdivided into vials, each containing 2 ml. of the solution. The vials are then lyophilized and sealed under nitrogen. Each vial contains 25 mg. of calcium glucoheptonate and 3 mg. of stannous chloride dihydrate.

EXAMPLE 2

Method of Using Blood Pool Imaging Kit

A solution of sodium chloride for injection USP (2 ml.) is added to a vial containing a lyophilized mixture of 3 mg. of stannous chloride dihydrate and 25.0 mg. calcium glucoheptonate. The resulting solution is used for the intravenous injection of patients for the purpose of imaging the blood pools for diagnostic purposes. The amount of solution used is based on the weight of the patient and sufficient volume is used so that 30 mcg./kg. of stannous ion, measured as stannous chloride dihydrate, is injected. It is recommended that no more than the contents of one vial be administered to any patient. After waiting a period of 30 minutes, a sterile saline solution of sodium pertechnetate-Tc99m (2–20mCi) is injected. This tags the red blood cells and permits imaging of the blood pools of the patient being examined almost immediately (from 30 seconds to 2 minutes).

What is claimed is:

1. A method of imaging blood pools in patients suspected of having cardiovascular abnormalities which comprises the steps of
    (1) intravenous injection of a solution comprising a water soluble, non-toxic, pharmaceutically acceptable salt of ketoglucoheptonic acid and a water soluble, non-toxic stannous salt;
    (2) waiting a period of 30 minutes; and
    (3) intravenous injection of a sterile saline solution containing from 2–20 mCi of sodium pertechnetate-Tc99m.

2. A method of imaging blood pools according to claim 1 wherein said glucoheptonate salt used is calcium glucoheptonate and said stannous salt is stannous chloride dihydrate.

3. A method of imaging blood pools according to claim 2 wherein the solution to be injected contains from 2.5–4 mg. of stannous salt, measured as stannous chloride dihydrate, and 25 mg. of calcium glucoheptonate.

4. A method of imaging blood pools according to claim 3 wherein the solution to be injected contains 3 mg. of stannous salt, measured as stannous chloride dihydrate, and 25 mg. of calcium glucoheptonate.

* * * * *